US009555217B2

(12) United States Patent
Shibata et al.

(10) Patent No.: US 9,555,217 B2
(45) Date of Patent: Jan. 31, 2017

(54) CATHETER

(71) Applicant: Terumo Kabushiki Kaisha, Shibuya-ku (JP)

(72) Inventors: Hideaki Shibata, Ashigarakami-gun (JP); Naoki Ishii, Ashigarakami-gun (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 661 days.

(21) Appl. No.: 13/755,912

(22) Filed: Jan. 31, 2013

(65) Prior Publication Data

US 2013/0197454 A1 Aug. 1, 2013

Related U.S. Application Data

(60) Provisional application No. 61/592,962, filed on Jan. 31, 2012.

(51) Int. Cl.
*A61M 25/00* (2006.01)
*A61M 25/04* (2006.01)

(52) U.S. Cl.
CPC ......... *A61M 25/0045* (2013.01); *A61M 25/04* (2013.01); *A61M 25/0009* (2013.01); *A61M 25/0041* (2013.01); *A61M 2025/006* (2013.01)

(58) Field of Classification Search
CPC .............. A61M 25/04; A61M 25/0041; A61M 25/0009; A61M 2025/006; A61M 25/0045
USPC ........... 604/264, 95.05, 506, 523, 528, 510, 530, 604/175
See application file for complete search history.

(56) References Cited

U.S. PATENT DOCUMENTS

| | | | | |
|---|---|---|---|---|
| 4,465,072 A | * | 8/1984 | Taheri | A61B 17/22 600/569 |
| 5,007,897 A | * | 4/1991 | Kalb et al. | 604/43 |
| 5,848,987 A | | 12/1998 | Baudino et al. | |
| 5,984,896 A | * | 11/1999 | Boyd | 604/175 |
| 7,212,869 B2 | * | 5/2007 | Wahlstrom et al. | 607/126 |
| 2005/0171588 A1 | | 8/2005 | Wahlstrom et al. | |
| 2006/0200111 A1 | * | 9/2006 | Moehle | A61M 25/0009 604/539 |

(Continued)

FOREIGN PATENT DOCUMENTS

EP 0339799 A2 11/1989
EP 2110147 A1 10/2009

(Continued)

OTHER PUBLICATIONS

Notification of Transmittal of the International Search Report and the Written Opinion of the International Searching Authority, or the Declaration (PCT/ISA/220), PCT International Search Report (PCT/ISA/210), Written Opinion of the International Searching Authority (Form PCT/ISA/237) issued on Mar. 19, 2013, in corresponding International Application No. PCT/JP2013/052249. (7 pages).

(Continued)

*Primary Examiner* — Bhisma Mehta
*Assistant Examiner* — Hamza Darb
(74) *Attorney, Agent, or Firm* — Buchanan Ingersoll & Rooney PC

(57) ABSTRACT

The catheter includes a hollow shaft, at least one adhering portion provided on an outer surface of the shaft, and plural protrusions arranged on the adhering portion. The protrusions are configured to increase a contact surface area to show adhesive strength due to a Van der Waals force.

14 Claims, 14 Drawing Sheets

(56) References Cited

U.S. PATENT DOCUMENTS

2008/0169059 A1    7/2008   Messersmith et al.
2010/0312324 A1   12/2010   Adden et al.

FOREIGN PATENT DOCUMENTS

| EP | 2258323 A1 | 12/2010 |
|---|---|---|
| GB | 1301393 | 12/1972 |
| JP | 2006-230442 A | 9/2006 |
| JP | 2010-125227 A | 6/2010 |
| JP | 2010125228 A | 6/2010 |
| WO | 99-29362 A1 | 6/1999 |
| WO | 2005-042646 A2 | 5/2005 |
| WO | 2009-126550 A2 | 10/2009 |
| WO | 2010/061680 A1 | 6/2010 |

OTHER PUBLICATIONS

Chinese Official Action Report in corresponding Chinese Patent Application No. 201380004712.4, mailed Nov. 4, 2015; 10 pages.
The extended European Search Report issued on Aug. 24 2015, by the European Patent Office in corresponding European Application No. 13743062.5. (10 pages).

\* cited by examiner

Axial direction →

(Proximal end side)    (Distal end side)

CATHETER

CROSS-REFERENCE TO RELATED APPLICATION

This application is based on U.S. Provisional Application No. 61/592,962 filed on Jan. 31, 2012, the contents of which are incorporated herein by reference.

BACKGROUND

1. Technical Field

The present invention relates to a catheter, and particularly relates to a catheter configured to be inserted into a blood vessel for use.

2. Description of the Related Art

Recently, percutaneous transluminal coronary angioplasty (PTCA) has been performed to treat a stenosis in a coronary artery. In PTCA, by using the Seldinger technique or the like, a guidewire for a guiding catheter is inserted into an arterial vessel, and along the guidewire, a guiding catheter is introduced into the arterial vessel. Then, with the guidewire preceding the guiding catheter, the tip of the catheter is positioned at the entrance to a coronary artery. Next, only the guidewire is taken out and a thinner guidewire for a balloon catheter is inserted into the guiding catheter to allow the tip thereof to reach a position beyond a stenotic site. After that, a proximal end of the guidewire is inserted into a lumen of a balloon catheter from a distal end side thereof, and the balloon catheter is advanced along the guidewire until a balloon in a deflated state is positioned at the stenotic site. Then, the balloon is inflated to expand the stenotic site, restoring blood flow on the distal end side farther than the stenotic site.

In this way, the guiding catheter serves to introduce a guidewire for a balloon catheter and a balloon catheter to a coronary artery entrance. The tip of the guiding catheter needs to be engaged at the coronary artery entrance. However, upon insertion of the guidewire and the balloon catheter into the coronary artery, a counterforce acts on the guiding catheter, which may cause the guiding catheter to be displaced from the coronary artery entrance. Thus, there has been known a method for maintaining the tip position of a guiding catheter at a coronary artery entrance (for example, see: Japanese Patent Application Laid-Open Publication No. 2006-230442). In this method, a shaft of the guiding catheter is made of a relatively hard resin and curved into shape, and the curved portion of the catheter is pressed against the inner surface of the blood vessel to push itself thereagainst.

However, even with the structure of pushing against the inner surface of the vessel by the curved portion, it is difficult to prevent completely the displacement of the tip position of the guiding catheter from the coronary artery entrance.

SUMMARY

The present invention has been accomplished to solve the problem, and it is an object of the invention to provide a catheter that can favorably maintain a state of being fixed in a body lumen.

A catheter for achieving the object is a catheter including a hollow shaft, at least one adhering portion provided on an outer surface of the shaft, and a plurality of protrusions arranged on the adhering portion, in which the protrusions are configured to increase a contact surface area to show adhesive strength due to a Van der Waals force.

The catheter thus formed has, on the outer surface of the shaft, the adhering portion with the protrusions showing adhesive strength due to the Van der Waals force. As the result, it allows the shaft to adhere to the inner surface of a body lumen so as to maintain favorably a fixed position thereof. Furthermore, since the protrusions show adhesive strength due to the Van der Waals force, the adhesive strength can be shown even in wet conditions, such as in a blood vessel.

The shaft may be formed to have a curved portion that is curved into shape. As the result, the shaft can be fixed in a manner pushing itself against the inner surface of the body lumen, and simultaneously the adhering portion allows the shaft to be fixed thereagainst more strongly.

The adhering portion may be provided in plurality in an axial direction of the shaft. This allows further increase in fixing strength.

The at least one adhering portion may be provided on an axially distal end side of the shaft. This allows the tip of the shaft to be fixed in a desirable position.

The at least one adhering portion may be provided partially in a circumferential direction of the shaft. As the result, rotation of the shaft can switch the state of the adhering portion between a state of being in contact with the inner surface of the body lumen and a state of being not in contact therewith, improving the manipulability of the catheter.

The at least one adhering portion may be provided on an outer part protruded by curving on an outer surface of the curved portion of the shaft that is curved into shape. This allows the outer part of the curved portion to be adhered and fixed to the inner surface of the body lumen so as to produce stably a pushing force against the inner surface thereof. Thus, the shaft can be fixed more stably.

The at least one adhering portion may be provided in a concave portion formed on the outer surface of the shaft. This allows the adhering portion to be housed in the concave portion when the shaft extends roughly linearly. Accordingly, the adhering portion is not allowed to show the adhesive strength until the shaft comes into a curved state, thereby improving the manipulability of the catheter.

The protrusions may be inclined to extend in the axial direction of the shaft. As the result, axial movement of the catheter allows the adhering portion to be adhered to or detached from the inner surface of the body lumen, thus improving the manipulability.

The protrusions may be inclined to extend in the circumferential direction of the shaft. As the result, circumferential movement of the catheter allows the adhering portion to be adhered to or detached from the inner surface of the body lumen, thus improving the manipulability.

The at least one adhering portion may be coated with a hydrophilic coating. As the result, the adhering portion can show good adhesive strength even in wet conditions.

The shaft and a first adhering portion and a second adhering portion (61 and 62 in FIG. 1) may be made of any one selected from a group consisting of silicone rubber, nitrile rubber, butyl rubber, and any combination thereof. This allows the adhering portions to show sufficiently fixing strength in the blood vessel, as well as the flexible material of the shaft can minimize negative influences on a living body.

The objects, features, and characteristics of this invention other than those set forth above will become apparent from the description given herein below with reference to preferred embodiments illustrated in the drawings.

DETAILED DESCRIPTION

The embodiment of this invention will be described below with reference to the drawings.

For convenience of explanation, the proportions of the drawings may be magnified and different from actual ones thereof.

A catheter according to an embodiment of the present invention is a Judkins-type guiding catheter 1 serving to introduce a balloon catheter to the entrance of the left coronary artery.

Figure 1:
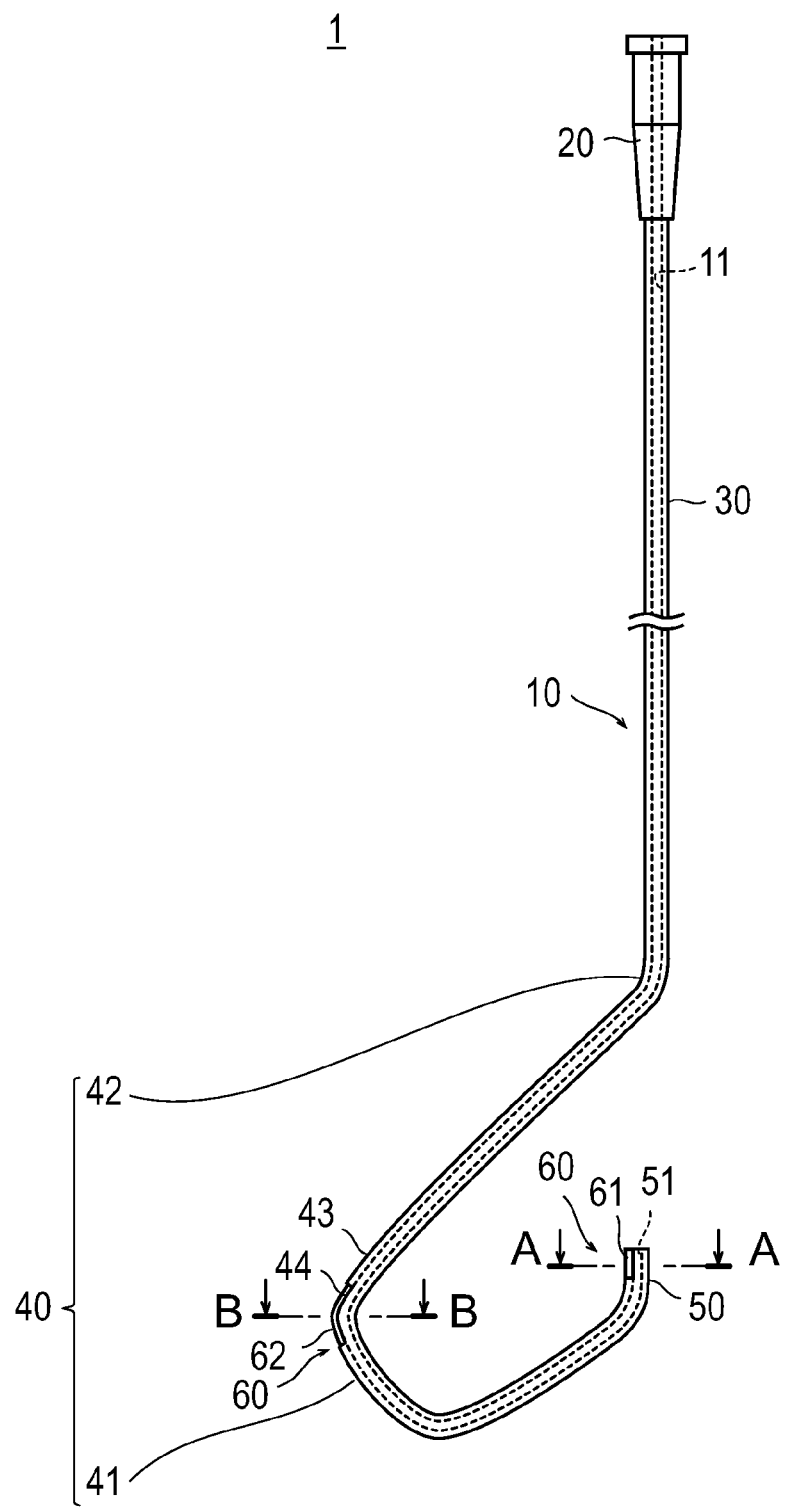
FIG. 1 is a plain view for explaining a guiding catheter according to an embodiment of the present invention.

As shown in FIG. 1, the guiding catheter 1 includes a shaft 10 adapted to be inserted into a blood vessel M and a hub 20 provided on the proximal end side of the shaft 10 and manipulated by a user's hands. Inside the shaft 10 with the hub 20 is formed a lumen 11 communicating therethrough. Hereinafter, in the guiding catheter 1, a side thereof having the shaft 10 adapted to be inserted into the blood vessel M is referred to as distal end side, and a side thereof having the hub 20 positioned on the side of the user's hands is referred to as proximal end side.

The shaft 10 includes a shaft proximal end 30 extending linearly from the hub 20, a curved portion 40 provided on the distal end side of the shaft proximal end 30 and curved into shape, and a tip portion 50 provided on the distal end side of the curved portion 40 and having an opening portion 51 of the lumen 11.

The curved portion 40 includes a first curved portion 41 provided on the distal side and a second curved portion 42 provided on the proximal end side farther than the first curved portion 41 and curved in an opposite direction from the first curved portion 41. On an outer part 43 protruded by curving on an outer surface of the first curved portion 41, there is formed a concave portion 44 by recessing down to be lower by one step than the outer surface of the shaft 10.

In addition, on the outer surface of the shaft 10 is provided an adhering portion 60 adapted to be adhered to the inner surface of the blood vessel M. The adhering portion 60 includes a first adhering portion 61 provided at the tip portion 50 and a second adhering portion 62 provided in the concave portion 44 of the first curved portion 41.

Figure 2:
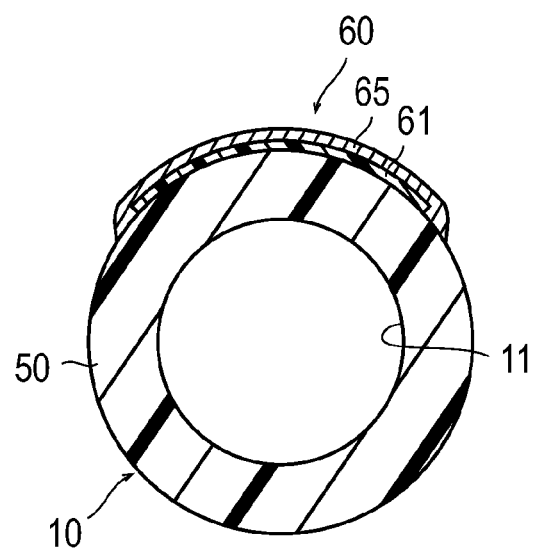
FIG. 2 is a cross-sectional view taken along line A-A of FIG. 1.

As shown in FIG. 2, the first adhering portion 61 is provided only partially on the tip portion 50 in a circumferential direction thereof, and not provided entirely in the circumferential direction thereof. A range for providing the first adhering portion 61 is preferably in a range of more than 25 degrees and less than 360 degrees in the circumferential direction thereof, so that while being arranged only partially in the circumferential direction, the first adhering portion 61 can still show favorable adhesive strength. However, this is merely one example. Additionally, the range therefor is preferably in a length of 1 to 10 mm axially, although not limited thereto.

Figure 3:
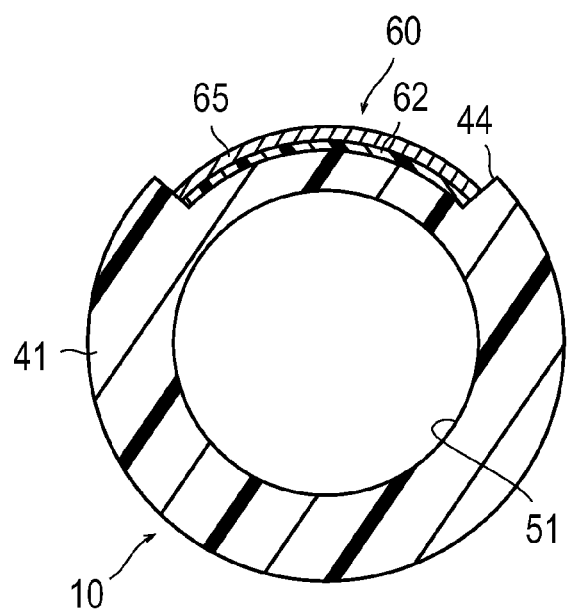
FIG. 3 is a cross-sectional view taken along line B-B of FIG. 1.

As shown in FIG. 3, the second adhering portion 62 is provided only in the concave portion 44 of the first curved portion 41 and only partially in a circumferential direction thereof, but not entirely in the circumferential direction thereof. The range for providing the second adhering portion 62 is preferably in a range of more than 25 degrees and less than 360 degrees in the circumferential direction thereof, so that while being arranged only partially in the circumferential direction, the second adhering portion 62 can still show favorable adhesive strength. However, this is merely one example. Additionally, the range therefor is preferably in a length of 5 to 40 mm axially, although not limited thereto.

The shaft 10 has flexibility and made of, for example, a polyolefin, such as polyethylene, polypropylene, polybutene, an ethylene-propylene copolymer, an ethylene-vinyl acetate copolymer, an ionomer, or a mixture of two or more kinds thereof, a thermoplastic resin such as a soft polyvinyl chloride resin, polyamide, a polyamide elastomer, polyester, a polyester elastomer, polyurethane, a fluorinated resin, or an acrylic resin, silicone rubber, or latex rubber.

The hub 20 is made of, for example, a thermoplastic resin such as polycarbonate, polyamide, polysulfone, polyarylate, a methacrylate-butylene-styrene copolymer.

Figure 4:
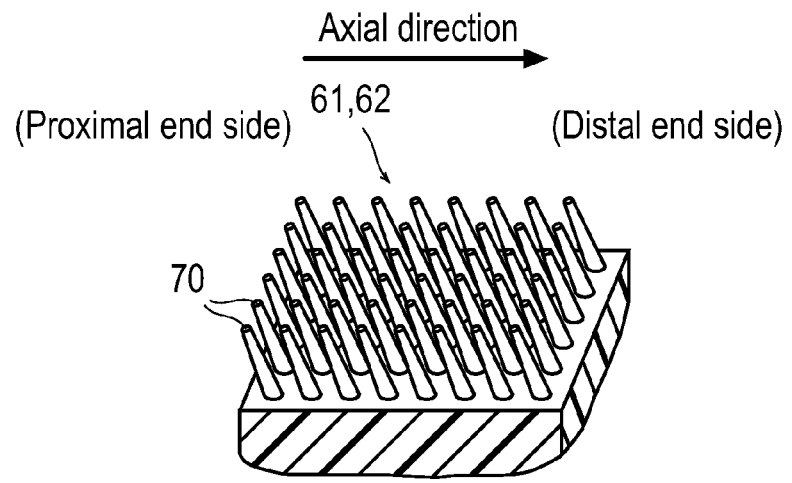
FIG. 4 is an enlarged perspective view illustrating an adhering portion.
Figure 5:
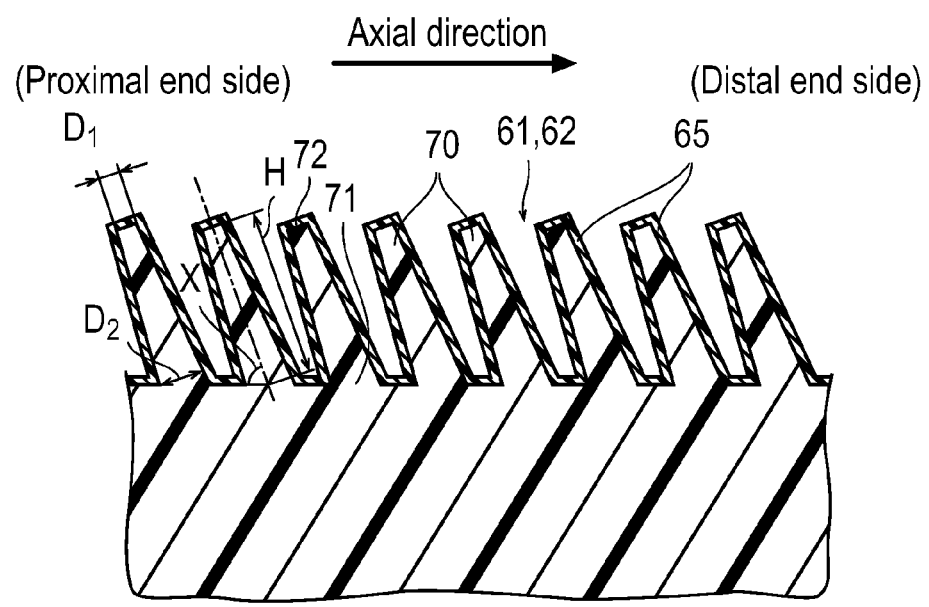
FIG. 5 is a cross-sectional view illustrating the adhering portion.

The first adhering portion 61 and the second adhering portion 62 both include a plurality of micro protrusions 70 with a size of micrometer to nanometer order, as shown in FIGS. 4 and 5.

Each of the plurality of the protrusions 70 provided on the first adhering portion 61 and the second adhering portion 62 is formed to be inclined in the axial direction of the shaft 10 in such a manner as to extend toward the proximal end side. An inclination angle X of the protrusions 70 with respect to the outer surface of the shaft 10 is set as needed and not specifically limited. However, the inclination angle X thereof may be set to 10 to 60 degrees, and preferably 15 to 45 degrees. The inclination direction and the inclination angle may be varied depending on each of the protrusions 70.

When the adhering portion 60 having the micro protrusions 70 formed thereon is closely adhered to the inner surface of the blood vessel M to be pressed thereagainst, the adhesion state can be maintained by utilizing a Van der Waals force between the micro protrusions 70 and the blood vessel M, without using any additional adhesive. For example, a diameter $D_2$ of a base portion 71 and a diameter $D_1$ of a top portion 72 of the each protrusion 70 is 5 nm to 10 μm; a height H of the each protrusion 70 is 1 to 500 μm; and a formation density thereof is 1 or more per 100 $μm^2$, thereby allowing high-density formation of the micro protrusions 70. The maximum outer diameter mentioned above represents a length of the longest part on a cross section orthogonal to the extension direction (protrusion direction) of the protrusion 70 and can be used even if the cross section is not necessarily circular. By providing the micro protrusion 70 in plurality to increase a surface area of the adhering portion 60, the Van der Waals force is produced that has a magnitude allowing the adhering portion 60 to maintain the state of being adhered to an adhesion target site. The adhesion mechanism is exerted not only in gas but also in liquid (wet conditions). A commonly known example of the adhesive structure using the Van der Waals force is a structure with micro fibers that can be seen on the soles of a gecko's feet.

An arrangement pattern of the protrusions 70 is not specifically limited. In the present embodiment, the protrusions 70 are arranged in a regular pattern, but may be arranged in an irregular pattern.

In addition, the protrusions 70 in the present embodiment have a truncated cone shape. However, the shape of the protrusions 70 is not limited, and, for example, may be a columnar shape with a polygonal cross section, or may be of the same cross section from the base portion 71 to the top portion 72. Alternatively, the cross section of the top portion 72 may be made larger than that of the base portion 71.

As a material for forming the protrusions 70, there may be used carbon nanotubes formed by a bottom-up method, a thermoplastic resin as a common plastic, a thermosetting polymer such as rubber, or a thermally crosslinkable polymer. Specific examples of the material for the protrusions 70 include polyesters such as polyethylene terephthalate and polybutylene terephthalate, as well as polyester elastomers including such polyesters as hard segments; polyolefins such as polyethylene and polypropylene, and polyolefin elastomers; copolymeric polyolefins produced using metallocene catalysts; vinyl-based polymers such as polyvinyl chloride, polyvinylidene chloride (PVDC), and poly(vinylidene fluoride) (PVDF); nylon-containing polyamides and polyamide elastomers (PAE); various thermoplastic resins such as polyimide, polystyrene, SEBS resins, polyurethane, polyurethane elastomers, ABS resins, acrylic resins, polyarylate, polycarbonate, polyoxymethylene (POM), polyvinyl alcohol (PVA), fluorinated resins (ethylene tetrafluoroethylene (ETFE), perfluoroalkoxy (PFA), or polytetrafluoroethylene (PTFE)), saponified ethylene-vinyl acetate, ethylene-copoly-vinyl alcohol, ethylene vinyl acetate, carboxymethyl cellulose, methylcellulose, cellulose acetate, polyvinyl sulfone, a liquid crystal polymer (LCP), polyether sulfone (PES), polyether ether ketone (PEEK), polyphenylene oxide (PPO), and polyphenylene sulfide (PPS), and high polymer derivatives thereof; silicone-based resins such as silicone rubber, nitrile rubber, butyl rubber, vulcanized rubber, polydimethyl siloxane (PMDS), and polyvinyl silane (PVS); thermosetting or crosslinkable polymers, such as epoxy resins and two-component polyurethane resins. Furthermore, there may be used polymer alloys containing any of the thermoplastic resins and the thermosetting or crosslinkable polymers. As a molding material, a resin solution prepared by dissolving a resin in a liquid may be used.

As shown in FIG. 5, the first and the second adhering portions 61 and 62 may be coated with a hydrophilic coating 65. As the result, the adhering portions can show more strong adhesive strength even in wet conditions, such as in blood.

The hydrophilic coating 65 is, for example, a copolymer of N-[2-(3,4-dihydroxyphenyl)ethyl](meth)acrylamide and 2-methoxyethyl(meth)acrylate, such as a copolymer (p(DMA-MEA)) of N-[2-(3,4-dihydroxyphenyl)ethyl]methacrylamide (DMA) and 2-methoxyethyl acrylate (MEA), although not limited thereto. Other examples that may be used as the hydrophilic coating 65 include dihydroxyphenyl alanine (DOPA)-based adhesives, mussel-based adhesives, polysaccharide-based adhesives, hyaluronic acid, collagen gel, collagen-based adhesives, alginate gel, crosslinked alginate, gelatin-resorcin-formalin-based adhesives, chitosan, transglutaminase, poly(amino acid)-based adhesives, cellulose-based adhesives, synthesized acrylic acid-based adhesives, polyacrylamide and derivatives thereof, polyacrylic acid and derivatives thereof, poly(methacrylic acid) and derivatives thereof, polyvinylpyrrolidone and derivatives thereof, polyethylene glycol-based adhesives, Matrigel, fibrin adhesives, fibrin clot, monostearoyl/glycerol/co-succinate (MGSA), a monostearoyl-glycerol-co-succinate/polyethylene glycol (MGSA/PEG) copolymer, laminin, elastin, proteoglycan, and compounds consisting of combinations thereof.

Figure 6A:
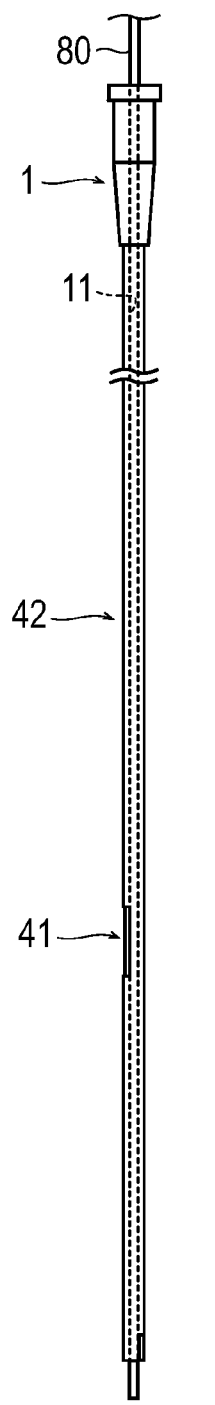
FIG. 6A is a plain view illustrating the guiding catheter according to the embodiment, in which a guidewire is inserted therethrough.
Figure 6B:
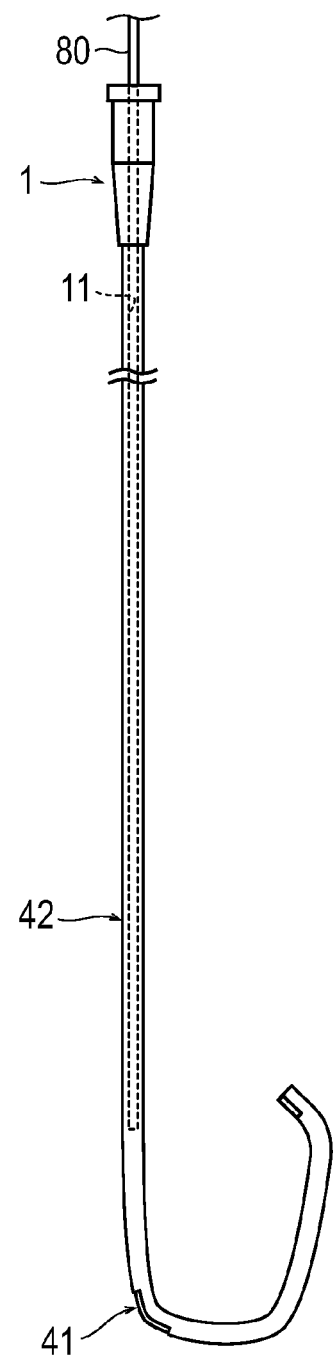
FIG. 6B is a plain view of the guiding catheter in which the guidewire is withdrawn partway.
Figure 6C:
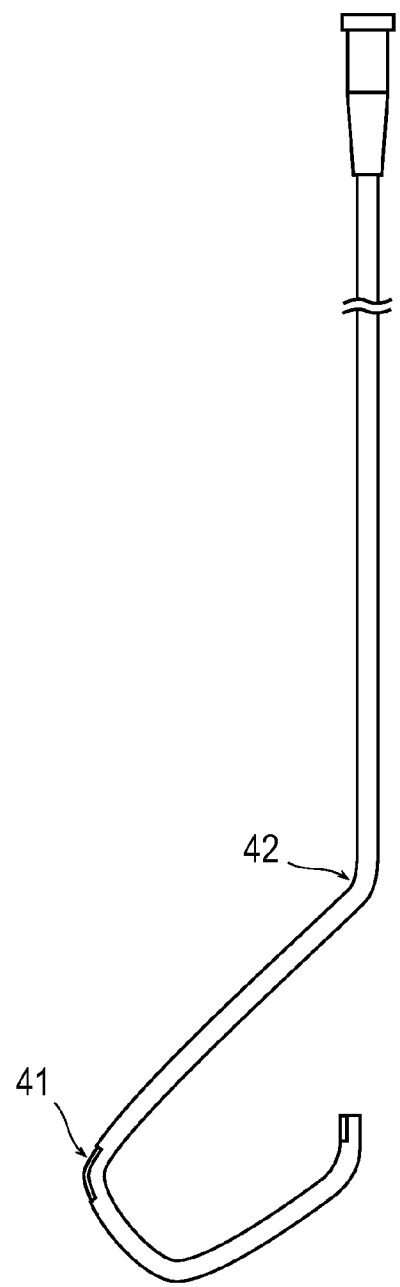
FIG. 6C is a plain view of the guiding catheter in which the guidewire has been completely withdrawn.

As shown in FIG. 1, the guiding catheter 1 is formed to be curved by the first curved portion 41 and the second curved portion 42. However, as shown in FIG. 6A, by inserting a guidewire 80 through the lumen 11, the first and the second curved portions 41 and 42 can be corrected into a roughly linear line. Then, when the guidewire 80 is withdrawn from the lumen 11 to the proximal end side and a distal end of the guidewire 80 is moved to the proximal end side farther than the first curved portion 41, the first curved portion 41 returns to the curved state thereof, as shown in FIG. 6B. When the guidewire 80 is further withdrawn from the lumen 11 to the proximal end side and the distal end of the guidewire 80 is moved to the proximal end side farther than the second curved portion 42, the second curved portion 42 also returns to the curved state thereof, in addition to the first curved portion 41, as shown in FIG. 6C.

Next, a description will be given of a method for producing protrusions 70 made of resin, as one example of a method for producing the protrusions 70.

Figure 7:
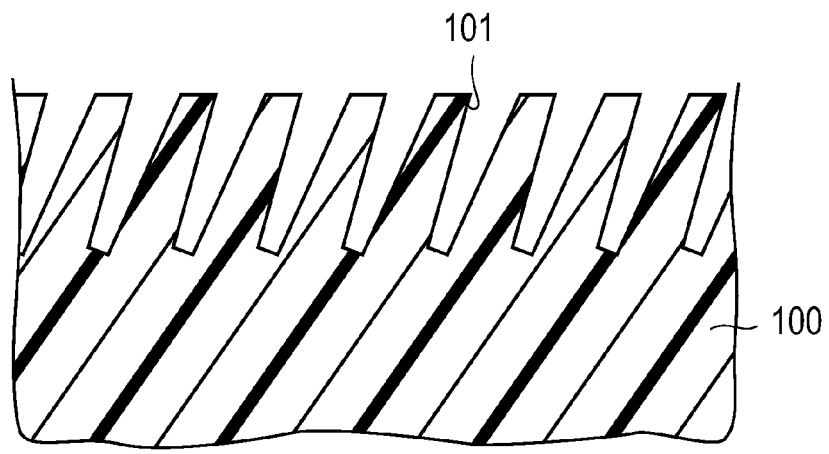
FIG. 7 is a cross-sectional view illustrating a mold for producing protrusions.

First, on a polymethylmethacrylate (PMMA) resin supported on a silicon wafer is formed a micro pattern 101 with several hundred nanometer-order holes by electron-beam lithography to produce a mold 100 (see FIG. 7). The shape of the micro pattern 101 is determined so as to correspond to a shape obtained by transcribing the protrusions 70 intended to be produced.

Next, as the material of the protrusions 70, any of the above-mentioned resin materials is dissolved in a liquid in an amount of 0.001 to 1% by weight to obtain a sol phase. The liquid may be chloroform or the like.

Figure 8:
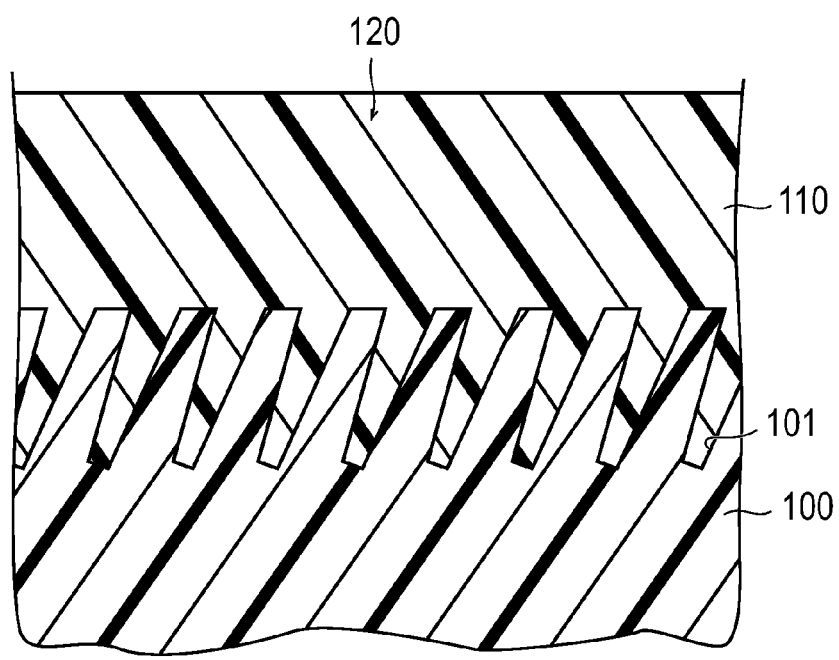
FIG. 8 is a cross-sectional view illustrating a state in which a material has been flown into the mold.

Next, the mold 100 is horizontally placed such that the surface thereof having the micro pattern 101 formed thereon faces upward. Then, as shown in FIG. 8, the material of the sol phase is flown into the mold 100 to introduce the material into the micro pattern 101, and is additionally flown thereinto by an amount equivalent to a thickness corresponding to a substrate 110 with a predetermined thickness. After that, the mold 100 is heated to a temperature of from room temperature to 40° C. to volatilize the liquid, thereby solidifying the material. When the material is thermoplastic, the material may be flown into the mold 100 after being dissolved by heating, and cooled down to be solidified.

Figure 9:
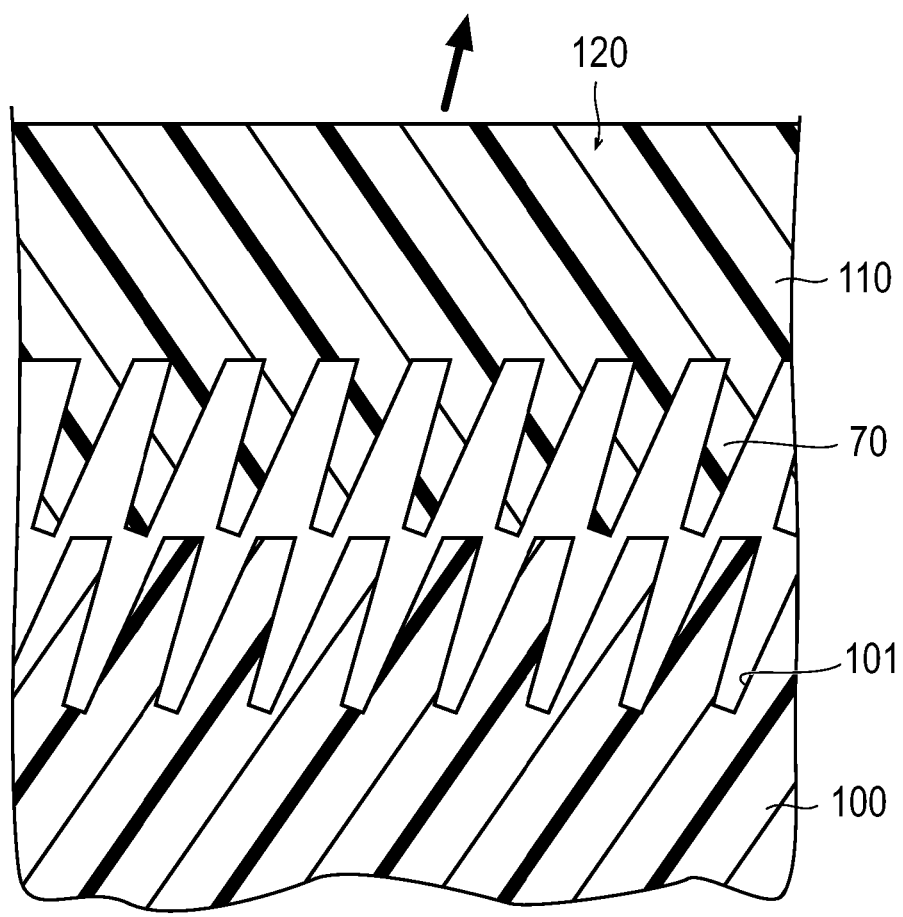
FIG. 9 is a cross-sectional view illustrating a state in which the protrusions are detached from the mold.

After solidifying the material, as shown in FIG. 9, the solidified material is taken out from the mold 100 to obtain a sheet 120 with a plurality of protrusions 70 formed on the substrate 110. Then, on the outer surfaces of the tip portion 50 and the concave portion 44 of the shaft 10 is adhered a small piece cut out in an appropriate size from the sheet 120, so as to form the first adhering portion 61 and the second adhering portion 62. The protrusions 70 may be formed integrally with the shaft 10, simultaneously with the formation of the shaft 10.

Fabrication of nano-order pattern may be performed by not only the method described above but also any other method such as a nano-imprint technique, laser, soft lithography, shaping using a micro bit (for example, a diamond bit), dispensing, or an inkjet method, for example. The fabrication method is preferably selected appropriately according to conditions such as the shape, size, and material of the protrusions. When the pattern has a pyramidal shape, the pattern can be easily fabricated by forming grooves lengthwise and crosswise using a micro bit.

Alternatively, the protrusions 70 may be formed using a femtosecond laser. The femtosecond laser is a laser whose pulse duration is ultra-shortened to the order of femtoseconds (one femtosecond is one quadrillionth of a second). Since the femtosecond laser applies energy to a target material for fabrication for an extremely short time (femtoseconds), fabrication can be performed before thermal conduction to a region other than a laser irradiation point occurs, so that more micro fabrication can be done. The femtosecond laser is applied to a sample in a scanning manner to produce a microstructure surface. Additionally, it is characteristic that femtosecond laser irradiation with linearly polarized light allows the self-organized formation of a microstructure pattern. Accordingly, the characteristics can be utilized to produce a microstructure surface.

Next, a description will be given of a manipulation using the guiding catheter 1 according to the preset embodiment, with reference to an example of percutaneous transluminal coronary angioplasty by transradial approach.

Figure 10:
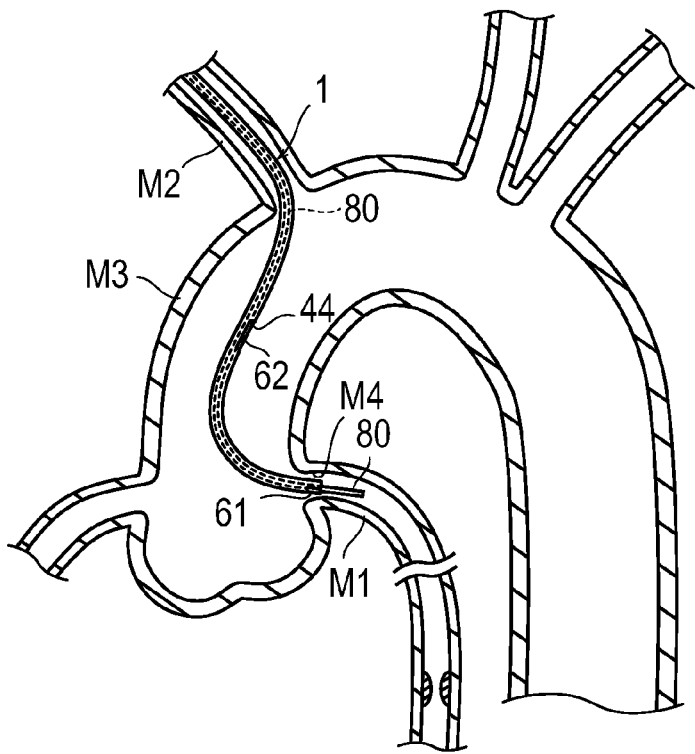
FIG. 10 is a cross-sectional view for explaining a state in which the guiding catheter has been introduced in the left coronary artery along the guidewire.
Figure 11:
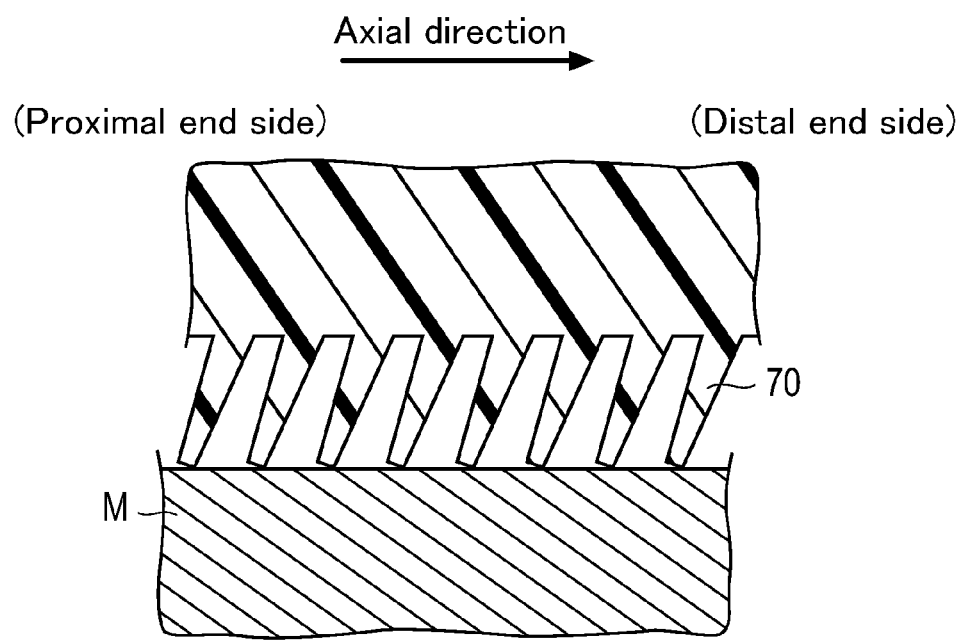
FIG. 11 is a cross-sectional view for explaining a state in which the guiding catheter is inserted into a blood vessel.

In the percutaneous transluminal coronary angioplasty, the guidewire 80 for a guiding catheter is inserted into a radial artery by the Seldinger technique or the like, and along the guidewire 80, the guiding catheter 1 is inserted into the radial artery. Then, with the guidewire 80 preceding the catheter 1, the guiding catheter 1 is advanced, and, as shown in FIG. 10, through a brachiocephalic artery M2 and an aortic arch M3, the tip portion 50 thereof is inserted into the entrance of a left coronary artery M1. At that time, the first adhering portion 61 is positioned so as to be oriented to an opposite side from a site M4 for adhesion located at the entrance of the left coronary artery M1. In this situation, due to the insertion of the guidewire 80 in the guiding catheter 1, curves of the first and the second curved portions 41 and 42 are in a roughly linearly corrected state (see FIG. 6A). Then, the position of the first adhering portion 61 can be adjusted until the first adhering portion 61 comes into a desirable adhesion state, without being adhered to the site M4 of the left coronary artery M1. When the guiding catheter 1 is advanced in the blood vessel M, the tips of the protrusions 70 slip on the inner surface of the blood vessel M, as shown in FIG. 11, and thus do not show large adhesive strength, due to the inclination of the protrusions 70 of the first and the second adhering portions 61 and 62 toward the proximal end side. In addition, the second adhering portion 62 is formed in the concave portion 44. In a state in which the guidewire 80 is present in the lumen 11, the first curved portion 41 is roughly linearly extended to allow the second adhering portion 62 to be housed in the concave portion 44. Accordingly, the second adhering portion 62 can hardly contact with the inner surface of the blood vessel M and hardly shows adhesive strength.

Figure 12:
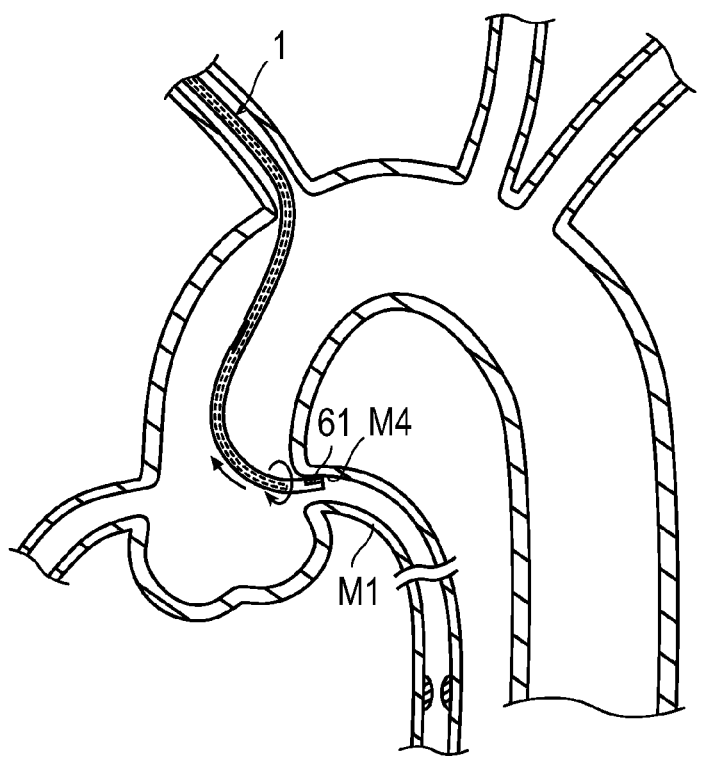
FIG. 12 is a cross-sectional view for explaining a state in which a first adhering portion of the guiding catheter is adhered to an entrance of the left coronary artery.

Next, as shown in FIG. 12, the hub 20 is manipulated to rotate the guiding catheter 1 by approximately 180 degrees, so that the first adhering portion 61 comes into contact with the adhesion site M4 at the entrance of the left coronary artery M1. Then, the guiding catheter 1 is withdrawn in the proximal end direction and thereby the first adhering portion 61 moves back in a state of being pressed against the entrance of the left coronary artery M1, as shown by an arrow in FIG. 13. At that time, a contact area with the left coronary artery M1 is large due to the tip shape of the protrusions 70 arranged at the first adhering portion 61. As a result, the first adhering portion 61 is adhered to the inner surface of the left coronary artery M1 by the Van der Waals force. In addition, due to the tip shape of the protrusions 70 inclined to extend toward the proximal end side, the guiding catheter 1 hardly slips in the direction toward the proximal end side, in contrast to the advancement thereof toward the distal end side, thus suppressing the displacement of the guiding catheter 1 from the entrance of the left coronary artery M1. In addition, the first adhering portion 61 may be coated with the hydrophilic coating 65, so that the first adhering portion 61 can show stronger adhesive strength even in wet conditions.

Figure 14:
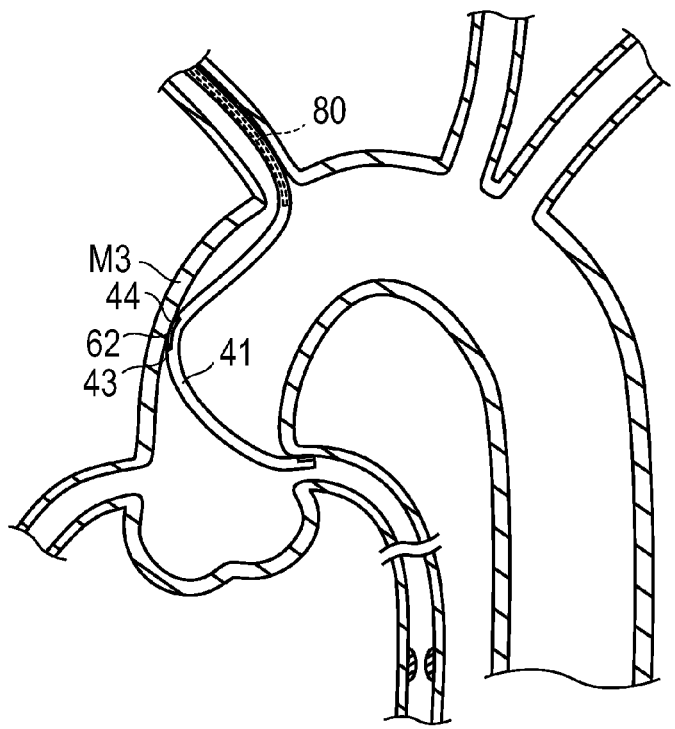
FIG. 14 is a cross-sectional view for explaining a state in which a second adhering portion of the guiding catheter is adhered to an aortic arch.
Figure 15:
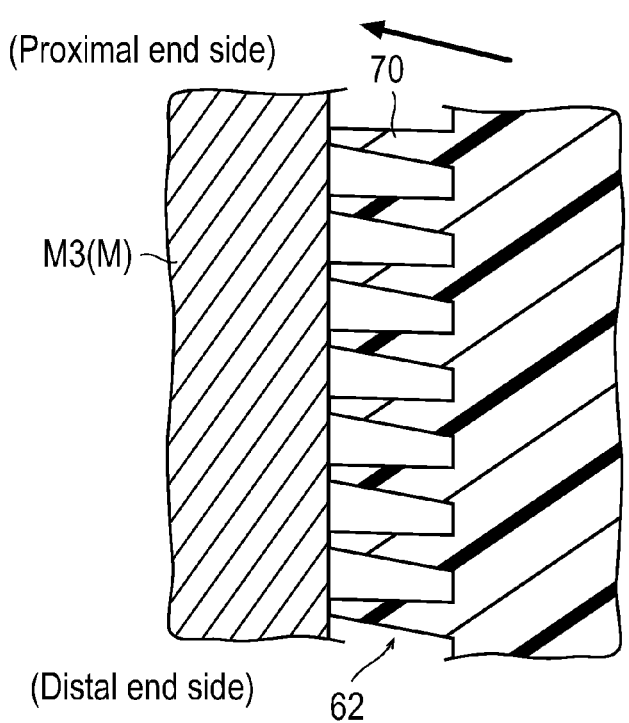
FIG. 15 is a cross-sectional view illustrating the second adhering portion of the guiding catheter in the state in which the second adhering portion is adhered to the aortic arch.

Next, by moving the guidewire 80 back to the proximal end side farther than the first curved portion 41, the first curved portion 41, which was roughly linearly corrected by the guidewire 80, is curved, as shown in FIG. 14. The first curved portion 14 includes the concave portion 44 on the outer part 43 configured to protrude by curving, and the second adhering portion 62 is formed in the concave portion 44, so that the second adhering portion 62 protrudes from the concave portion 44 to come in contact with an inner surface of the aortic arch M3 by a counterforce of the shaft 10. Additionally, under the condition, by manipulating the hub 20 to withdraw the shaft 10 back to the proximal end side, the protrusions 70 come in contact with the aortic arch M3 on a large area, as shown in FIG. 15. As a result, the second adhering portion 62 is adhered to the inner surface of the aortic arch M3 by the Van der Waals force. Furthermore, the second adhering portion 62 may be coated with the hydrophilic coating 65, so as to show stronger adhesive strength even in wet conditions.

Figure 16:
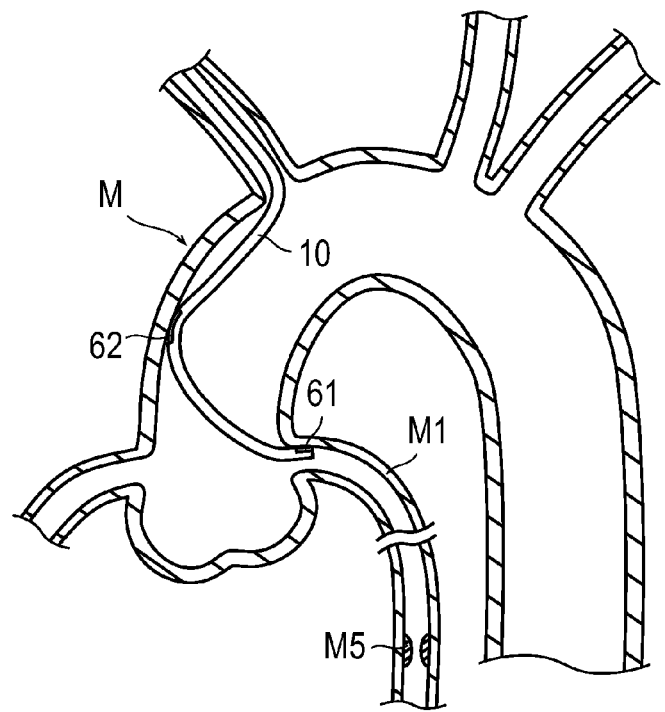
FIG. 16 is a cross-sectional view for explaining a state in which the guidewire has been withdrawn from the guiding catheter.

After this, when the guidewire 80 is completely pulled out, the guiding catheter 1 is fixed in the blood vessel M by the shaped shaft 10 in a state of pushing itself against the inner surface thereof, and the first and the second adhering portions 61 and 62 are adhered to the inner surface thereof, as shown in FIG. 16. This can favorably maintain the state in which the opening portion 51 at the distal end of the shaft 10 is engaged at the entrance of the left coronary artery M1.

Figure 17:
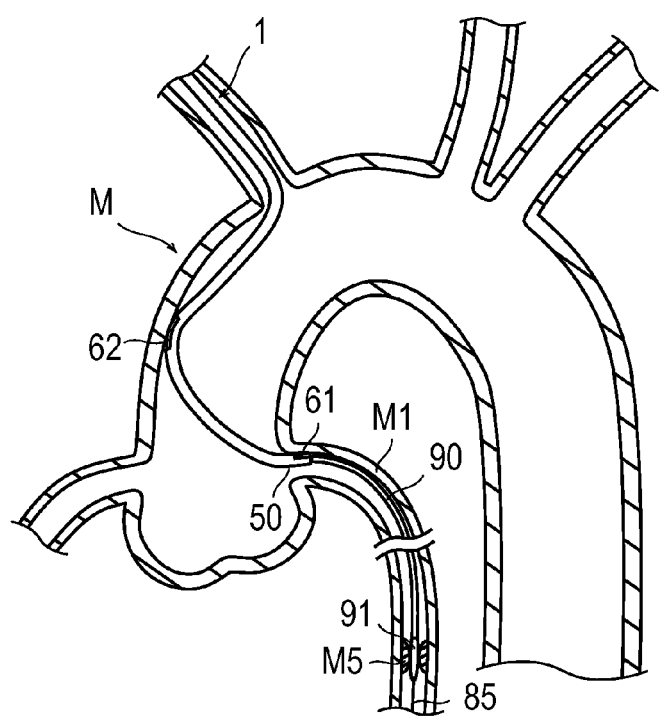
FIG. 17 is a cross-sectional view for explaining a state in which a balloon catheter has been inserted through the guiding catheter into the left coronary artery.

Next, a thinner guidewire 85 for a balloon catheter 90 is inserted into the guiding catheter 1 to allow the tip thereof to reach a position beyond a stenotic site M5 formed in the left coronary artery M1. After that, a proximal end portion of the guidewire 85 is inserted into a lumen of the balloon catheter 90 from a distal side thereof to advance the balloon catheter 90 along the guidewire 85, then, as shown in FIG. 17, allowing a balloon 91 in a deflated state to be positioned at the stenotic site M5. Upon the advancement of the guidewire 85 and the balloon catheter 90 in the left coronary artery M1 as described above, a counterforce acts on the guiding catheter 1. However, since the guiding catheter 1 is strongly fixed in the blood vessel M by the force of the shaft 10 pushing against the inner surface thereof and the first and the second adhering portions 61 and 62, the tip portion 50 of the guiding catheter 1 is favorably maintained without detaching from the entrance of the left coronary artery M1, preventing the degradation of manipulability.

Figure 18:
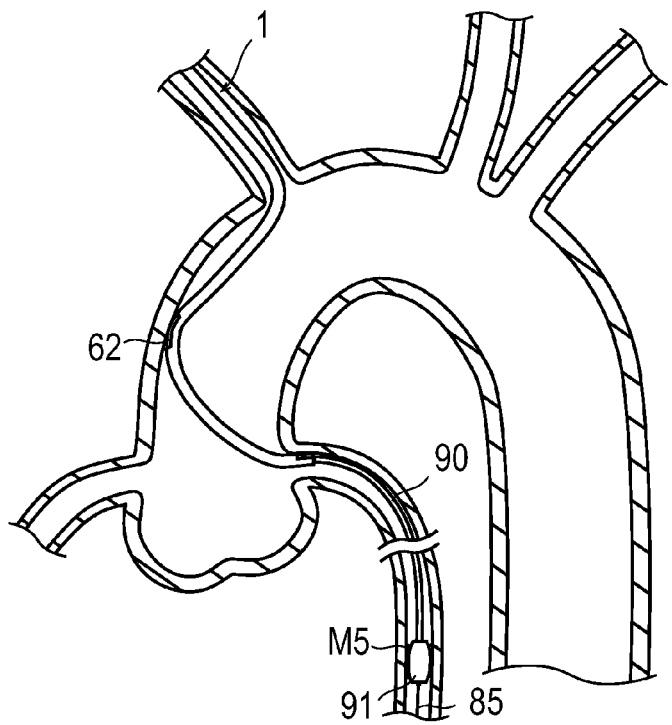
FIG. 18 is a cross-sectional view for explaining a state in which a balloon of the balloon catheter has been inflated to expand a stenotic site.

After this, as shown in FIG. 18, the balloon 91 is inflated to expand the stenotic site M5, securing blood flow to the distal side farther than the stenotic site M5. At that time, in addition to the expansion of the stenotic site M5 by the balloon 91, a stent may be expanded by the balloon 91 for indwelling.

Figure 13:
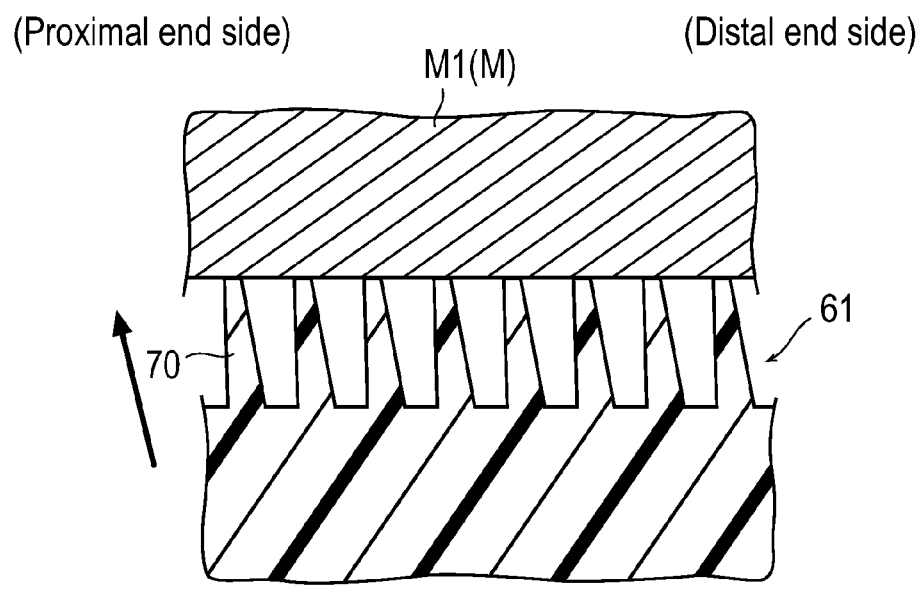
FIG. 13 is a cross-sectional view illustrating the first adhering portion of the guiding catheter in the state in which the first adhering portion is adhered to the entrance of the left coronary artery.
Figure 19:
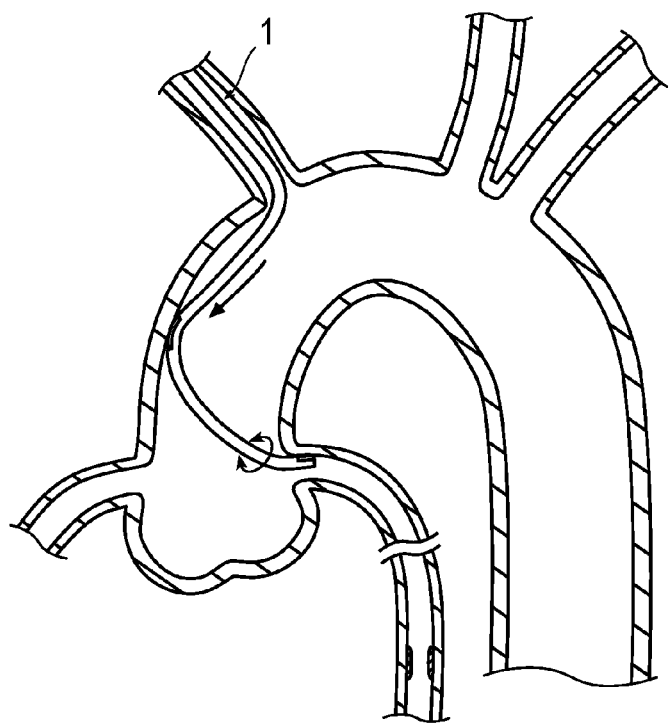
FIG. 19 is a cross-sectional view for explaining a state in which an adhering portion of the balloon catheter is detached from the inner surface of the blood vessel.
Figure 20:
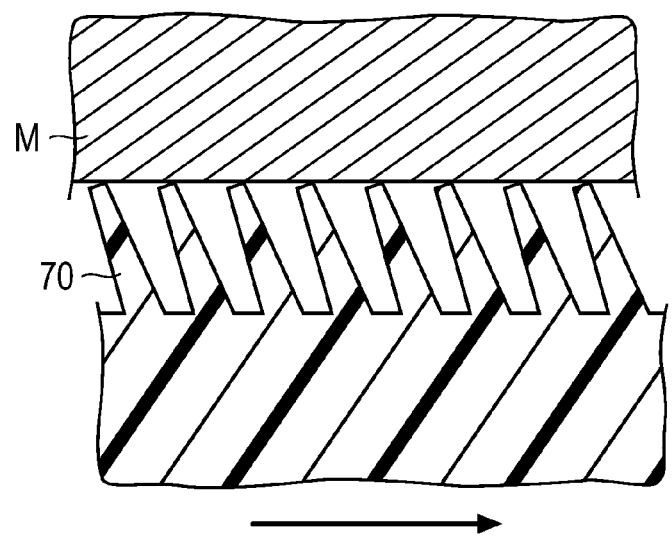
FIG. 20 is a cross-sectional view illustrating the state in which the adhering portion of the balloon catheter is detached from the inner surface of the blood vessel.

Next, after deflating the balloon 91, the guidewire 85 for the balloon catheter 90 and the balloon catheter 90 are together pulled out from the guiding catheter 1. Then, as shown in FIG. 19, the hub 20 is manipulated to thrust and/or rotate the guiding catheter 1. As the result, the protrusions 70, which were pressed against and adhered to the inner surface of the blood vessel M, as shown in FIGS. 13 and 15, are subjected to a force in a direction returning to the original shape thereof, as shown in FIG. 20. As the result, the protrusions 70 are detached from the inner surface of the blood vessel M, releasing the adhesion. In this situation, due to the inclined formation of the protrusions 70, the protrusions 70 can be detached by a weak force from the thrusting action and/or rotation action. This can minimize negative influences on the living body.

Figure 21:
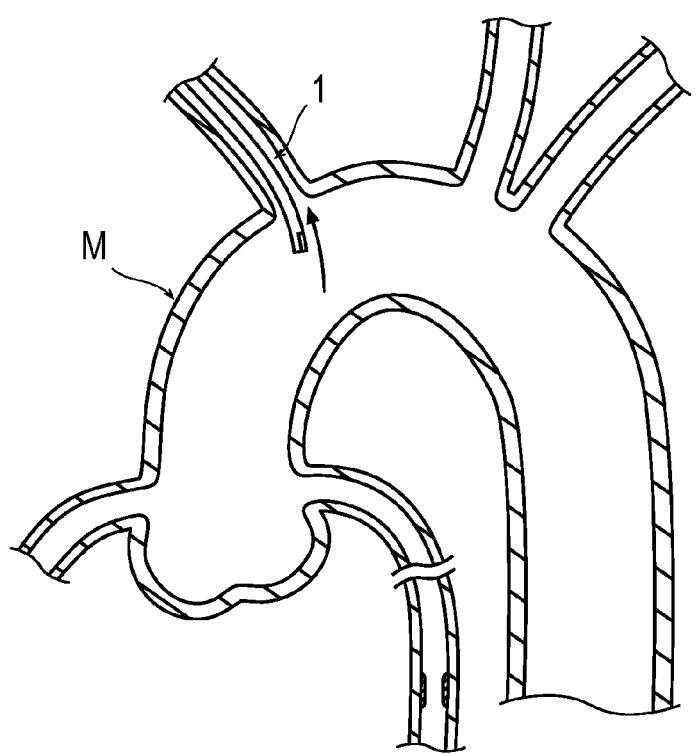
FIG. 21 is a cross-sectional view for explaining a state in which the balloon catheter is withdrawn from inside the blood vessel.

After this, as shown in FIG. 21, the guiding catheter 1 is pulled out from the blood vessel M to complete the manipulation.

In the guiding catheter 1 according to the present embodiment, the first and the second adhering portions 61 and 62 having the plurality of protrusions 70 are provided on the shaft 10 and the protrusions 70 are configured to increase the contact surface area to show adhesive strength due to the Van der Waals force, so that the fixation of the catheter in the blood vessel M can be favorably maintained. In addition, by allowing the force to act in a predetermined direction, the first and the second adhering portions 61 and 62 can be easily detached from the inner surface of the blood vessel M. Furthermore, since the adhesion is retained by the Van der Waals force, a large retention force can be produced despite the small pressing force, reducing negative influences on the living body. Moreover, the first and the second adhering portions 61 and 62 allow the adhesion and detachment, with minimum stress on the living body. Thus, when not retained at a desirable position upon adhesion, the first and the second adhering portions 61 and 62 can be once detached from the inner surface of the vessel to be retained again.

In addition, since the shaft 10 is provided with the first and the second curved portions 41 and 42 curved into shape, the shaft 10 can be fixed in the blood vessel M in the manner pushing itself against the inner surface thereof, as well as can be fixed more strongly in the blood vessel M by the first and the second adhering portions 61 and 62.

Additionally, the adhering portion 60 (the first adhering portion 61 and the second adhering portion 62) is provided in plurality in the axial direction of the shaft 10, thus further increasing fixing strength.

Additionally, since the first adhering portion 61 is provided on the axial distal end side of the shaft 10, the tip portion 50 of the shaft 10 can be fixed at a desirable position.

In addition, at least one of the first and the second adhering portions 61 and 62 is provided partially in the circumferential direction of the shaft 10. Thus, by rotation of the shaft 10, the adhering portion 60 can be switched between the state of being in contact with the inner surface of the blood vessel M and the state of being not in contact therewith, improving the manipulability of the catheter.

In addition, the second adhering portion 62 is provided on the outer part 43 configured to protrude by curving on the outer surface of the first curved portion 41 of the shaft 10 curved into shape. Thus, by allowing the outer part 43 to come in contact with the inner surface of the blood vessel M in the state of curving the first curved portion 41, the second adhering portion 62 can be adhered and fixed to the blood vessel M. This allows the force pushing against the inner surface thereof to be stably produced in the blood vessel M, so that the shaft 10 can be fixed more stably.

Additionally, since the second adhering portion 62 is provided in the concave portion 44 formed on the outer surface of the shaft 10, the second adhering portion 62 is housed in the concave portion 44 when the shaft 10 is roughly linearly extended. This allows the second adhering portion 62 not to show adhesive strength until the shaft 10 comes into the curved state, thus improving the manipulability.

Additionally, since the protrusions 70 are inclined to extend in the axial direction of the shaft 10, adhesion or detachment of the adhering portion 60 can be performed depending on the direction of manipulation (axial direction or rotation direction) of the guiding catheter 1, thus improving the manipulability.

In addition, by coating the adhering portion 60 with the hydrophilic coating 65, the adhering portion 60 can show favorable adhesive strength even in wet conditions.

Furthermore, the shaft 10 may be made of any one selected from a group consisting of silicone rubber, nitrile rubber, butyl rubber, and any combination thereof. In this case, the guiding catheter 1 becomes softer than a common guiding catheter 1 and thus the pushing force against the inner surface of the vessel is reduced, but the fixing strength in the blood vessel M can be sufficiently shown by the adhering portion 60, allowing the minimization of negative influences on the living body.

Furthermore, the first and the second adhering portions 61 and 62 may be formed by attaching a sheet or the like having an adhesive surface onto the first and the second curved portions of the shaft.

The present invention is not limited to the above-described embodiments alone, and various modifications can be made by those skilled in the art without departing from the technical idea of the invention. For example, the adhering portion having the plurality of protrusions may be one, three, or more. In addition, the adhering portion may be provided by splitting in the circumferential direction of the shaft. Alternatively, the adhering portion may be provided not partially but entirely in the circumferential direction thereof.

Figure 22:
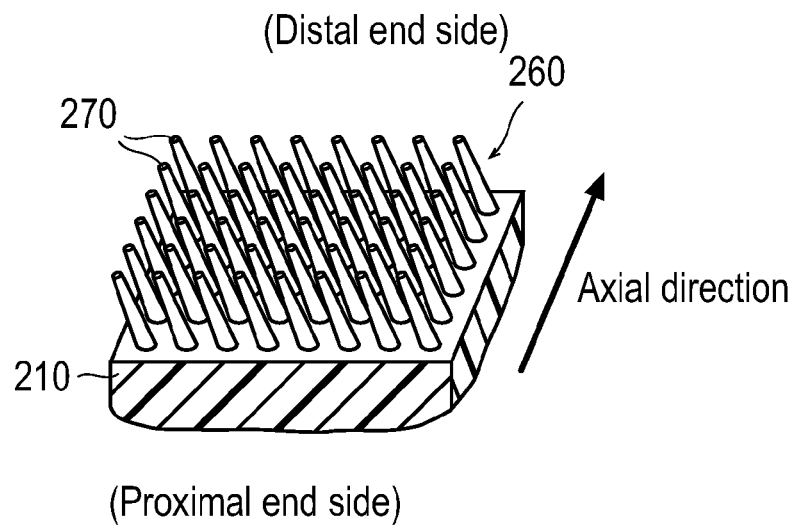
FIG. 22 is a perspective view illustrating an adhering portion of a modification of the guiding catheter according to the embodiment.

In addition, as shown in FIG. 22, protrusions 270 provided on an adhering portion 260 may be inclined to extend in a circumferential direction of a shaft 210. With the inclined extension of the protrusions 270 in the circumferential direction of the shaft 210, the adhering portion 260 can be adhered to or detached from the inner surface of the blood vessel M by rotation of the guiding catheter, thus improving the manipulability of the catheter.

Figure 23:
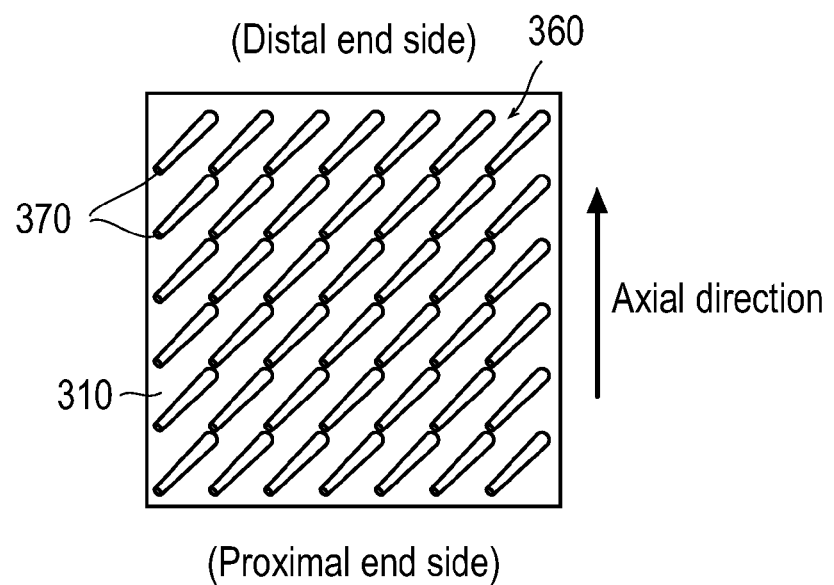
FIG. 23 is a perspective view illustrating an adhering portion of another modification of the guiding catheter according to the embodiment.

Furthermore, as shown in FIG. 23, protrusions 370 provided on an adhering portion 360 may be inclined to extend both in a circumferential direction and in an axial direction of a shaft 310. With the structure, the adhering portion 360 can be adhered to or detached from the inner surface of the blood vessel M by a movement of the guiding catheter either in the axial direction or in a rotation direction, thus improving the manipulability.

In addition, the inclination direction of the protrusions may be different depending on each of the protrusions provided in plurality. Additionally, the protrusions may be inclined to extend toward the distal end, or the protrusions may not be inclined. Furthermore, the inclination direction thereof may be irregular depending on the protrusion.

Figure 24:
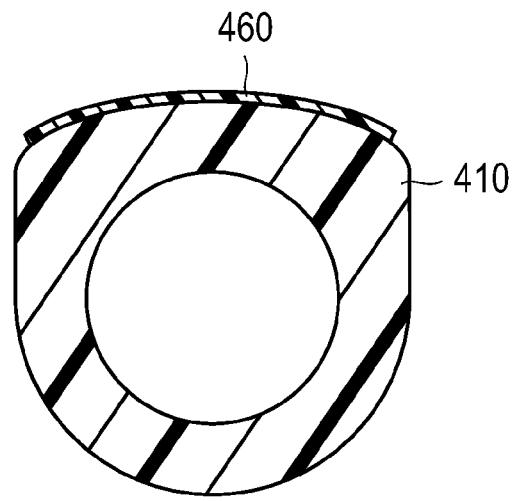
FIG. 24 is a cross-sectional view illustrating an adhering portion of still another modification of the guiding catheter according to the embodiment.

In addition, as shown in FIG. 24, a surface of a shaft 410 having an adhering portion 460 formed thereon may be flattened further than other portions of the shaft 410. As the result, a radius of curvature of the adhering portion 460 can be made close to that of the inner surface of the blood vessel M, facilitating the adhesion of the adhering portion 460 to the inner surface thereof.

Figure 25:
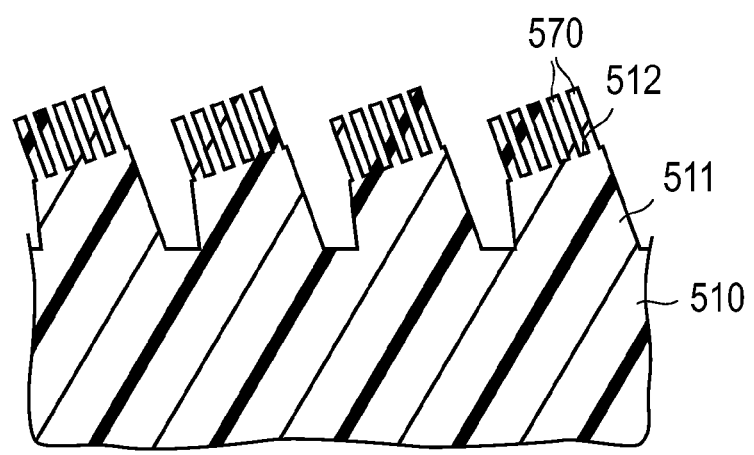
FIG. 25 is a cross-sectional view illustrating an adhering portion of yet another modification of the guiding catheter according to the embodiment.

Additionally, as shown in FIG. 25, a plurality of bases 511 protruding from a shaft 510 may be provided to form a plurality of protrusions 570 on the respective bases 511. In this case, by allowing top surfaces 512 of the bases 511 to be inclined with respect to an outer surface of the shaft 510 as shown in the figure, the protrusions 570 can be inclined with respect thereto. The top surfaces 512 of the bases 511 may be oriented parallel to the outer surface of the shaft 510, and the extension direction of the protrusions 570 is also not specifically limited.

In addition, the guiding catheter 1 according to the present embodiment is configured to be fixed in the left coronary artery M1, but may be configured to be fixed in the right coronary artery, or may be configured to be fixed in another site. The site to be fixed is not limited to any specific one. In addition, the guiding catheter 1 according to the present embodiment is the Judkins-type catheter, but may be an Amplatz-type catheter. The shape of the guiding catheter 1 is not specifically limited as long as it is a catheter having a portion to be fixed in a body lumen. An insertion site for approach does not have to be a radial artery and may be a femoral artery or the like.

In addition, the present invention is not limited to a guiding catheter alone and applicable to any other catheter configured to be fixed in a body lumen. For example, the invention may be applicable to an angiographic catheter configured to be fixed in a blood vessel to inject a contrast medium through an inner lumen and a catheter configured to be inserted into a body lumen, such as a vessel, other than a blood vessel.

What is claimed is:

1. A catheter comprising:
   a hollow shaft possessing a distal-most end, a proximal-most end, and a pre-shaped curved portion positioned proximal to the distal-most end;
   a first adhering portion and a second adhering portion, the first adhering portion and the second adhering portion each provided on an outer surface of the shaft;
   a plurality of protrusions arranged on the first adhering portion and the second adhering portion to increase, the plurality of protrusions being arrange in the first adhering portion and second adhering portions to increase a contact surface area to show adhesion strength due to a Van der Waals force;
   the first adhering portion being provided on an axially distal end side of the distal-most end of the hollow shaft, and
   the second adhering portion being provided in a recessed portion formed on the outer surface of the pre-shaped curved portion, the second adhering portion protruding from the outer surface when the pre-shaped curved portion is in a curved state, the pre-shaped curved portion possessing a concave-shaped inner part and a convex-shaped outer part, the recessed portion being located at the convex-shaped outer part.

2. The catheter according to claim 1, wherein the first adhering portion and the second adhering portion are provided in plurality in an axial direction of the shaft.

3. The catheter according to claim 1, wherein at least one of the first adhering portion and the second adhering portion is provided partially in a circumferential direction of the shaft.

4. The catheter according to claim 1, wherein the plurality of protrusions are inclined to extend in the axial direction of the shaft.

5. The catheter according to claim 1, wherein the plurality of protrusions are inclined to extend in the circumferential direction of the shaft.

6. The catheter according to claim 1, wherein the first adhering portion and the second adhering portion are coated with a hydrophilic coating.

7. The catheter according to claim 1, wherein the shaft, the first adhering portion, and the second adhering portion are made of any one selected from a group consisting of silicone rubber, nitrile rubber, butyl rubber, and any combination thereof.

8. The catheter according to claim 1, wherein the first adhering portion and the second adhering portion are provided by attaching a pre-formed adhesion sheet.

9. A catheter comprising:
   a hollow shaft possessing an outer surface and a convexly-shaped portion;
   the outer surface of the shaft including a recessed portion that is recessed relative to the outer surface of an adjoining portion of the shaft, the recessed portion being located at the convexly-shaped portion; and a plurality of outwardly projecting protrusions arranged in the recessed portion of the shaft and projecting outwardly of the recessed portion when the shaft is in a curved state, the plurality of outwardly projecting protrusions being arranged to increase a contact surface area to show adhesion strength due to a Van der Waals force.

10. The catheter according to claim 9, wherein the outer surface of the shaft includes a plurality of recessed portions, and a plurality of outwardly projecting protrusions arranged in each of the recessed portions.

11. The catheter according to claim 9, wherein the recessed portion is positioned at a distal end of the shaft.

12. The catheter according to claim 9, wherein the recessed portion possesses a circumferential extent less than 360°.

13. The catheter according to claim 9, wherein the plurality of protrusions are inclined to extend in an axial direction of the shaft.

14. The catheter according to claim 9, wherein the plurality of protrusions are inclined to extend in the circumferential direction of the shaft.

\* \* \* \* \*